US00PP30886P2

(12) United States Plant Patent
Kobayashi

(10) Patent No.: US PP30,886 P2
(45) Date of Patent: Sep. 17, 2019

(54) ***PETUNIA* PLANT NAMED 'DOPETSUNPEPU'**

(50) Latin Name: ***(Petunia* x *hybrida)* X *Calibrachoa* sp.**
Varietal Denomination: Dopetsunpepu

(71) Applicant: DUMMEN GROUP B.V., De Lier (NL)

(72) Inventor: Ruth Kobayashi, Carlsbad, CA (US)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/932,932

(22) Filed: May 23, 2018

(51) Int. Cl.
*A01H 5/02* (2018.01)
*A01H 6/82* (2018.01)

(52) U.S. Cl.
USPC ..... Plt./356.11
CPC ..... *A01H 6/824* (2018.05)

(58) Field of Classification Search
USPC ..... Plt./356.11
CPC ..... A01H 6/824; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Petunia* plant named 'Dopetsunpepu', characterized by its semi-mounding to semi-trailing plant habit; moderately vigorous to vigorous growth habit; freely branching habit; early and freely flowering habit; flowers that are red purple and pale yellow to white in color; and good garden performance.

2 Drawing Sheets

Botanical designation: (*Petunia* x *hybrida*) X *Calibrachoa* sp.
Cultivar denomination: 'DOPETSUNPEPU'.

CROSS-REFERENCED TO CLOSELY-RELATED APPLICATIONS

Title: *Petunia* Plant Named 'Duesunelapr'
Applicant: Ruth Kobayashi
Filed: Dec. 12, 2016
Ser. No.: 15/530,205
Grant date: Apr. 3, 2018
U.S. Plant Pat. No.: 29,188
Title: *Petunia* Plant Named 'Duesunpkmorn'
Applicant: Ruth Kobayashi
Filed: Dec. 12, 2016
Ser. No.: 15/530,203
Grant date: Apr. 3, 2018
U.S. Plant Pat. No.: 29,192
Title: *Petunia* Plant Named 'Duesunrose'
Applicant: Ruth Kobayashi
Filed: Dec. 12, 2016
Ser. No.: 15/530,204
Grant date: Apr. 3, 2018
U.S. Plant Pat. No.: 29,189
Title: *Petunia* Plant Named 'Duesunvan'
Applicant: Ruth Kobayashi
Filed: Dec. 12, 2016
Ser. No.: 15/530,202
Grant date: Mar. 27, 2018
U.S. Plant Pat. No.: 29,155

BACKGROUND OF THE INVENTION

The present invention relates to a new and distinct cultivar of *Petunia* plant, botanically known as (*Petunia* x *hybrida*) X *Calibrachoa* sp. and hereinafter referred to by the name 'Dopetsunpepu'.

The new *Petunia* plant is a product of a planned breeding program conducted by the Inventor in Encinitas, Calif. The objective of the breeding program is to create new moderately vigorous and semi-mounding *Petunia* plants with numerous attractive flowers.

The new *Petunia* plant is a naturally-occurring whole plant mutation of a proprietary selection of (*Petunia* x *hybrida*) X *Calibrachoa* sp. identified as code number TT-0814, not patented. The new *Petunia* plant was discovered and selected by the Inventor as a single flowering plant within a population of plants of the parent selection in a controlled greenhouse environment in Encinitas, Calif. on Nov. 11, 2015.

Asexual reproduction of the new *Petunia* plant by terminal vegetative cuttings in a controlled greenhouse environment in Encinitas, Calif. since Dec. 11, 2015 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dopetsunpepu'. These characteristics in combination distinguish 'Dopetsunpepu' as a new and distinct *Petunia* plant:

1. Semi-mounding to semi-trailing plant habit.
2. Moderately vigorous to vigorous growth habit.
3. Freely branching habit.
4. Early and freely flowering habit.

5. Flowers that are red purple and pale yellow to white in color.
6. Good garden performance.

Plants of the new *Petunia* can be compared to plants of the parent selection. Plants of the new *Petunia* differ primarily from plants of the parent selection in flower color as plants of the parent selection have salmon pink-colored flowers.

Plants of the new *Petunia* can be compared to plants of (*Petunia* x *hybrida*) X *Calibrachoa* sp. 'Duesunelapr', disclosed in U.S. Plant Pat. No. 29,188. Plants of the new *Petunia* differ primarily from plants of 'Duesunelapr' in flower color as plants of 'Duesunelapr' have greyed yellow-colored flowers with pink-colored margins.

Plants of the new *Petunia* can be compared to plants of (*Petunia* x *hybrida*) X *Calibrachoa* sp. 'Duesunpkmorn', disclosed in U.S. Plant Pat. No. 29,192. Plants of the new *Petunia* differ primarily from plants of 'Duesunpkmorn' in flower color as plants of 'Duesunpkmorn' have intense red purple-colored flowers with yellow green-colored centers.

Plants of the new *Petunia* can be compared to plants of (*Petunia* x *hybrida*) X *Calibrachoa* sp. 'Duesunrose', disclosed in U.S. Plant Pat. No. 29,189. Plants of the new *Petunia* differ primarily from plants of 'Duesunrose' in flower color as plants of 'Duesunrose' have bright red purple-colored flowers.

Plants of the new *Petunia* can be compared to plants of (*Petunia* x *hybrida*) X *Calibrachoa* sp. 'Duesunvan', disclosed in U.S. Plant Pat. No. 29,155. Plants of the new *Petunia* differ primarily from plants of 'Duesunvan' in flower color as plants of 'Duesunvan' have pale yellow tinged with light red-colored flowers.

Plants of the new *Petunia* can also be compared to plants of *Petunia* X *Calibrachoa* 'Dancalipet', disclosed in U.S. Plant Pat. No. 16,063. Plants of the new *Petunia* and 'Dancalipet' differ primarily in the following characteristics:

1. Plants of the new *Petunia* are semi-mounding to semi-trailing in plant habit whereas plants of 'Dancalipet' are mounding in plant habit.
2. Plants of the new *Petunia* are more vigorous than plants of 'Dancalipet'.
3. Plants of the new *Petunia* and 'Dancalipet' differ in flower color as plants of 'Dancalipet' have red purple-colored flowers.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph on the first sheet is a side perspective view of a typical flowering plant of 'Dopetsunpepu' grown in a container.

The photograph on the second sheet is a close-up view of a typical flowering plant of 'Dopetsunpepu'.

DETAILED BOTANICAL DESCRIPTION

The aforementioned photographs and following observations, measurements and values describe plants grown during the early spring in 15-cm containers in a polyethylene-covered greenhouse in Encinitas, Calif. and under cultural practices typical of commercial *Petunia* production. During the production of the plants, day temperatures averaged 25° C., night temperatures averaged 20° C. and light levels ranged from 4,000 lux to 4,500 lux. Plants were twelve weeks old when the photographs and description were taken. In the following description, color references are made to The Royal Horticultural Society Colour Chart, 2007 Edition, except where general terms of ordinary dictionary significance are used.

Botanical classification: (*Petunia* x *hybrida*) X *Calibrachoa* sp. 'Dopetsunpepu'.

Parentage: Naturally-occurring whole plant mutation of a proprietary selection of (*Petunia* x *hybrida*) X *Calibrachoa* sp. identified as code number TT-0814, not patented.

Propagation:

*Type*.—By terminal vegetative cuttings.

*Time to initiate roots, summer and winter*.—About five to seven days at night temperatures about 20° C.

*Time to produce a rooted young plant, summer and winter*.—About three weeks at night temperatures about 20° C.

*Root description*.—Fine, fibrous; typically white in color, actual color of the roots is dependent on substrate composition, water quality, fertilizers, substrate temperature and age of roots.

*Rooting habit*.—Freely branching; dense.

Plant description:

*Plant and growth habit*.—Semi-mounding to semi-trailing plant habit; freely branching habit with about four to six basal (primary) lateral branches, each primary lateral branch with secondary and tertiary laterals potentially developing at every node; moderately vigorous to vigorous growth habit.

*Plant height*.—About 25 cm.

*Plant diameter*.—About 46 cm.

Lateral branch description:

*Length*.—About 26 cm.

*Diameter*.—About 4 mm.

*Internode length*.—About 2.1 cm.

*Strength*.—Strong.

*Aspect*.—Initially upright then becoming outwardly trailing with development.

*Texture and luster*.—Pubescent, minute; matte.

*Color, developing and developed*.—Close to 144A.

Leaf description:

*Arrangement*.—Before flowering, alternate; after flowering, opposite; simple.

*Length*.—About 4.5 cm.

*Width*.—About 2 cm.

*Shape*.—Elliptical with ovate tendencies.

*Apex*.—Broadly acute.

*Base*.—Cuneate with attenuate tendencies.

*Margin*.—Entire.

*Texture and luster, upper and lower surfaces*.—Pubescent, minute; slightly glossy.

*Venation pattern*.—Pinnate; arcuate.

*Color*.—Developing leaves, upper and lower surfaces: Close to 146B. Fully expanded leaves, upper surface: Close to N137A; venation, close to 146B. Fully expanded leaves, lower surface: Close to 146A; venation, close to 146B.

*Petioles*.—Length: About 4 mm. Diameter: About 2 mm. Strength: Moderately strong. Texture and luster, upper and lower surfaces: Pubescent, minute; slightly glossy. Color, upper and lower surfaces: Close to 146B.

Flower description:

*Flower type and flowering habit*.—Single salverform flowers arising from leaf axils; freely flowering habit with flowers potentially developing at every node and typically more than 500 flowers per plant will develop during the flowering season; flowers face upright to outwardly.

*Fragrance*.—None detected.

*Natural flowering season*.—Plants flower continuously during the summer in Southern California; early flowering habit, plants typically beginning flowering about seven weeks from unrooted cuttings.

*Flower longevity*.—Individual flowers last about four to seven days on the plant; flowers persistent.

*Flower buds* (*prior to petal appearance*).—Length: About 1.25 cm. Diameter: About 5 mm. Shape: Elongated. Texture and luster: Pubescent, minute; matte. Color: Close to 146B to 146C.

*Flower diameter*.—About 4 cm.

*Flower depth* (*height*).—About 2.75 cm.

*Flower throat diameter*.—About 9 mm.

*Flower tube length*.—About 1.75 cm.

*Flower tube diameter, middle*.—About 7 mm.

*Flower tube diameter, base*.—About 3 mm.

*Corolla*.—Arrangement: Five petals fused at the base and opening into a flared trumpet. Petal lobe length (from throat): About 1.6 cm. Petal lobe width: About 2 cm. Petal shape: Roughly spatulate. Petal apex: Rounded to truncate, occasionally with shallow indentation. Petal margin: Entire; moderately undulate. Petal texture and luster, upper surface: Smooth, glabrous; satiny; slightly glossy. Petal texture and luster, lower surface: Pubescent, minute; matte. Throat texture and luster: Smooth, glabrous; slightly glossy. Tube texture and luster: Pubescent, minute; matte. Color: Petal lobe, when opening, upper surface: Close to between N57A and 60A; towards the margins, close to 2D; towards the throat, close to between 7A and 9A. Petal lobe, when opening, lower surface: Close to between 58A and 60B; towards the margins, close to 4D. Petal lobe, fully opened, upper surface: Close to N57A to N57B; towards the margins, close to NN155A; towards the throat, close to 7A; ring around throat, close to N163A to N163B; midvein, close to N144A to N144B and lateral venation, similar to lamina colors; with development color becoming closer to between N57B to N57D and towards the margins, close to NN155A, white areas expanding with development. Petal lobe, fully opened, lower surface: Close to 58A and 58B; towards the margins, close to NN155A; venation, close to 146A to 146B; with development color becoming fainter than 58B and margins, close to NN155A; white areas expanding with development. Flower throat: Close to 12A; venation, close to 59A. Flower tube: Close to 144A to 144B; venation, close to 146A.

*Calyx*.—Arrangement: Five sepals fused at the base forming a star-shaped calyx. Calyx length: About 1.1 cm. Calyx diameter: About 2.1 cm. Sepal length: About 1.1 cm. Sepal width: About 3 mm. Sepal shape: Lanceolate. Sepal apex: Acute. Sepal margin: Entire. Sepal texture and luster, upper and lower surfaces: Pubescent, minute; matte. Color: When opening and fully opened, upper surface: Close to 146A. When opening and fully opened, lower surface: Close to 146A.

*Peduncles*.—Length: About 1.4 cm. Diameter: About 1 mm. Strength: Moderately strong. Aspect: About 45° from lateral stem axis. Texture and luster: Pubescent, minute; matte. Color: Close to 146A.

*Reproductive organs*.—Stamens: Quantity per flower: Five. Filament length: About 1.2 cm. Filament color: Close to 145D and NN155A. Anther length: Less than 1 mm. Anther shape: Nearly round. Anther color: Close to 6D. Pollen amount: None observed. Pistils: Quantity per flower: One. Pistil length: About 1.4 cm. Style length: About 1 cm. Style color: Close to 145D. Stigma diameter: About 1 mm. Stigma shape: Rounded. Stigma color: Close to 145A. Ovary color: Close to 145D. Seeds and fruits: Seed and fruit development have not been observed on plants of the new *Petunia* to date.

Garden performance: Plants of the new *Petunia* have been observed to have good garden performance and tolerate full sunlight conditions, wind, rain and temperatures ranging from about 5° C. to about 40° C.

Pathogen & pest resistance: Plants of the new *Petunia* have not been observed to be resistant to pathogens and pests common to *Petunia* plants to date.

It is claimed:

1. A new and distinct *Petunia* plant named 'Dopetsunpepu' as illustrated and described.

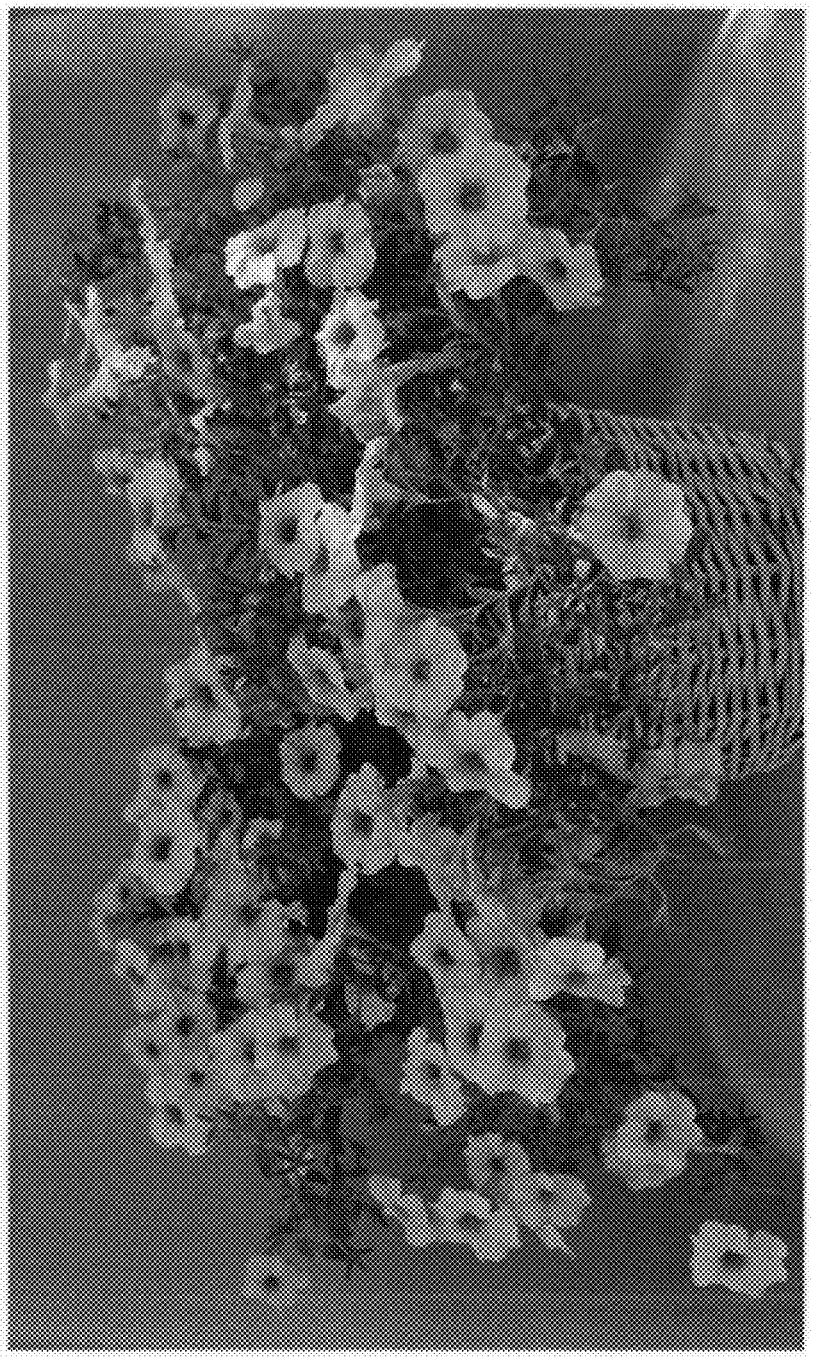

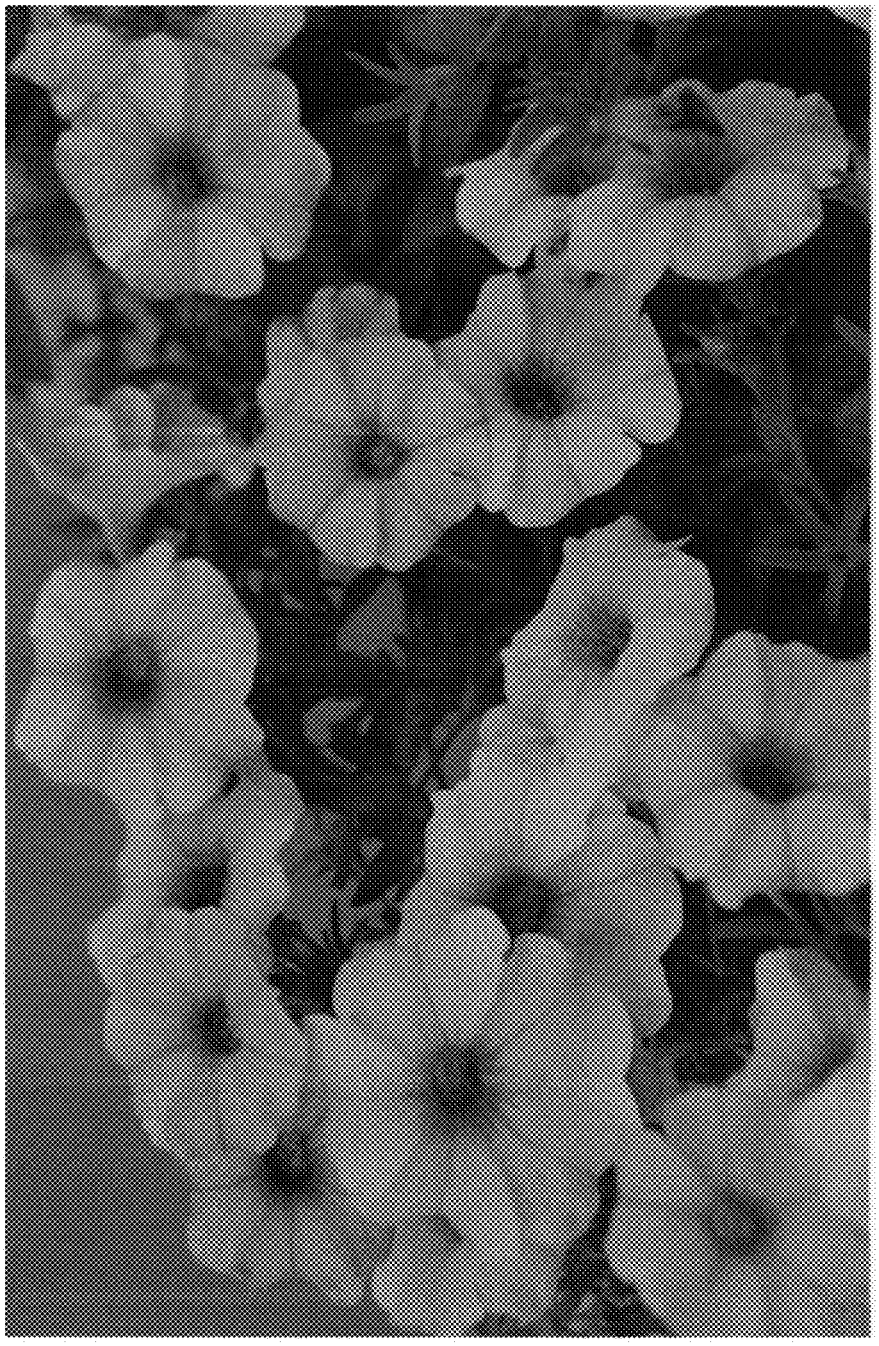

* * * * *